United States Patent [19]

Ichijo

[11] Patent Number: 4,548,603

[45] Date of Patent: Oct. 22, 1985

[54] SANITARY NAPKIN

[75] Inventor: Teruko Ichijo, Funabashi, Japan

[73] Assignee: I.P.C. Co., Ltd., Tokyo, Japan

[21] Appl. No.: 517,323

[22] Filed: Jul. 25, 1983

[30] Foreign Application Priority Data

Jul. 28, 1982 [JP] Japan .................................. 57-113469

[51] Int. Cl.⁴ ............................................. A61F 13/16
[52] U.S. Cl. ................................ 604/385 R; D24/49; 40/2 R
[58] Field of Search ....................... 604/385, 386, 375; 128/157; D24/49; 40/2 R

[56] References Cited

U.S. PATENT DOCUMENTS

D. 267,431 12/1982 Santarelli ............................. D24/49
3,329,145 7/1967 De Merre ....................... 604/375 X
3,547,120 12/1970 Grossman ........................... 128/157
3,842,837 10/1974 Sward ................................. 604/385

Primary Examiner—William H. Grieb
Attorney, Agent, or Firm—Fliesler, Dubb, Meyer & Lovejoy

[57] ABSTRACT

A sanitary napkin comprising an absorbent pad for absorbing the flow from vagina, a soft case for containing the absorbent pad therein, a patterned projection extended from one end of the soft case and bearing a symbolic pattern, and an engaging member provided at the other end of soft case for engagement with patterned projection. The sanitary napkin can be used without melancholy mood and can be disposed easily and cleanly by folding the napkin so as to conceal the flow.

4 Claims, 6 Drawing Figures

SANITARY NAPKIN

BACKGROUND OF THE INVENTION

1. Field of the Invention

The present invention relates to a sanitary napkin which is used to absorb the flow from vagina during menstruation.

2. Description of the Prior Art

Because of the recent tendency towards the intake of foods high in calories, children grow very quickly so that menarche or the first menstruation occurs at relatively earlier ages. It has not become infrequent that girls at the third or fourth grades experience menarche.

Each menstrual period is very troublesome for women and almost all the women are in a depressed mood during menstruation.

FIG. 1 shows a conventional sanitary napkin comprising a soft paper case or outer shell 1 with absorbent pad 2. The ends 3 and 4 of the soft paper case 1 are sealed. The appearance of such sanitary napkin is very uninteresting and flat so that young women feel more melancholy to use such a sanitary napkin.

SUMMARY OF THE INVENTION

In view of the above, one of the objects of the present invention is therefore to provide a sanitary napkin with which a woman may be relieved from a melancholic mood and may experience menstruation without distreess or inconvenience.

Another object of the present invention is to provide a sanitary napkin which provides a pleasant feeling to a user before she uses it and which is so structured as to be disposed easily and cleanly, while concealing the flow, once the sanitary napkin is used.

According to the present invention, there is provided a sanitary napkin comprising an absorbent pad for absorbing the flow from vagina, a soft case for containing the absorbent pad therein, a patterned projection extended from one end of the soft case and bearing a symbolic pattern or image, and an engaging member provided at the other end of the soft case for engagement with the patterned projection, whereby a woman can comfortably spends a menstruation period.

It is preferred that the engaging mamber may comprise a slit formed in the other end of the soft case, so that the patterned projection can be inserted into the slit.

It is also preferred that the outer surface of the soft case which does not contact a human body may have an image pattern. The outer surface may be colored with the image pattern.

Preferably, the outer surface of the soft case may be provided with an adhesive tape for preventing the slippage of the sanitary napkin.

DETAILED DESCRIPTION OF THE PREFERRED EMBODIMENTS

Figure 2:
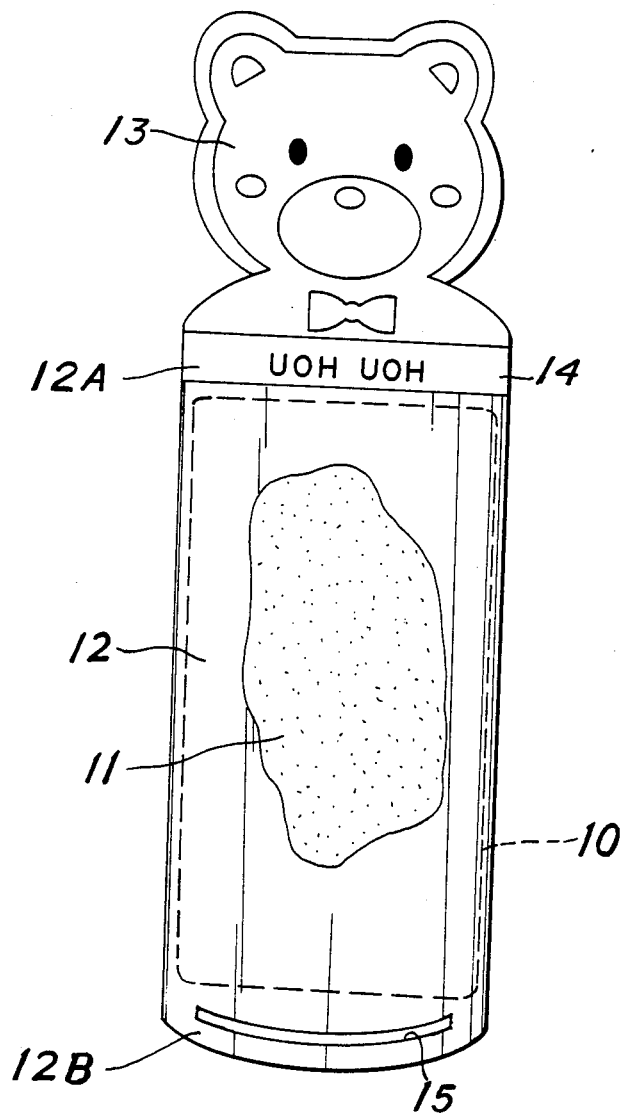
FIG. 2 is a front view showing, partly broken, a first embodiment of a sanitary napkin in accordance with the present invention.

In FIG. 2, there is shown a first embodiment of a sanitary napkin according to the present invention. The sanitary napkin comprises an absorbent pad 10 for absorbing the flow 11 from vagina. The size of the absorbent pad 10 is so selected as to fully cover the genital or sexual organs and the absorbent pad 10 is enclosed in a soft case 12 whose longitudinal ends 12A and 12B are sealed. A patterned projection 13 which represents a symbolic image or pattern is extended from one end or upper end 12A of the soft case 12.

For instance, in the case of the first embodiment shown in FIG. 2, the patterned projection 13 is in the form of the head of dog. The upper end 12A of the soft case 12 is provided with an image bearing portion 14 containing some picture, words or phrases. An engaging portion, for example, in the form of a slit 15 is formed in the lower end 12B of the soft case 10, so that the patterned projection 13 can be inserted into the slit 15 before and after the use. For instance, after the use, the sanitary napkin is folded in such a manner that the surface which absorbed the flow is folded inward and then the patterned projection 13 is inserted into the slit 15 for engagement. Thereafter, the folded sanitary napkin may be disposed.

The patterned projection 13 may be formed by stamping. Alternatively, a pattern, an image picture or the like may be printed. Further, in case that some picture is printed on the patterned projection 13, not only the projection 13 but also an entire or outer package may be sterilized in accordance with the regulations of some authority.

Figure 3:
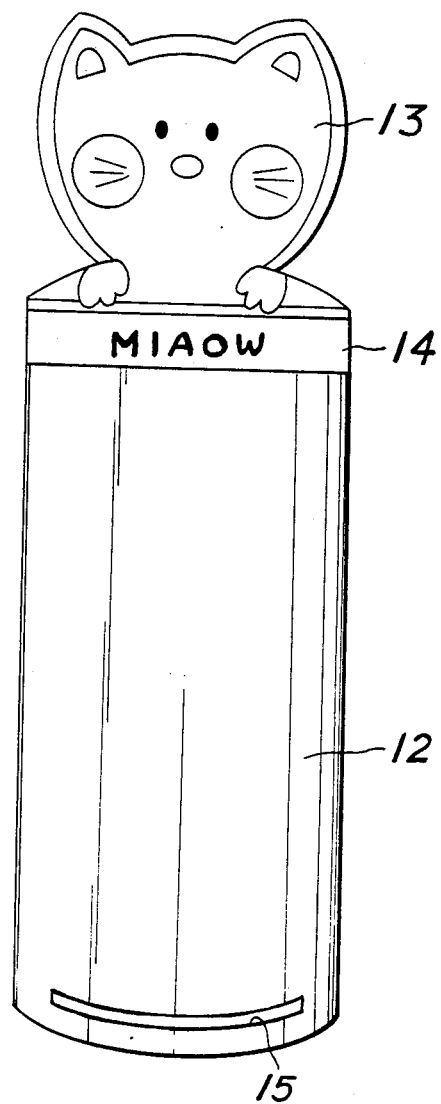
FIGS. 3 and 4 are front views showing, respectively, a second embodiment and a third embodiment in accordance with the present invention.
Figure 4:
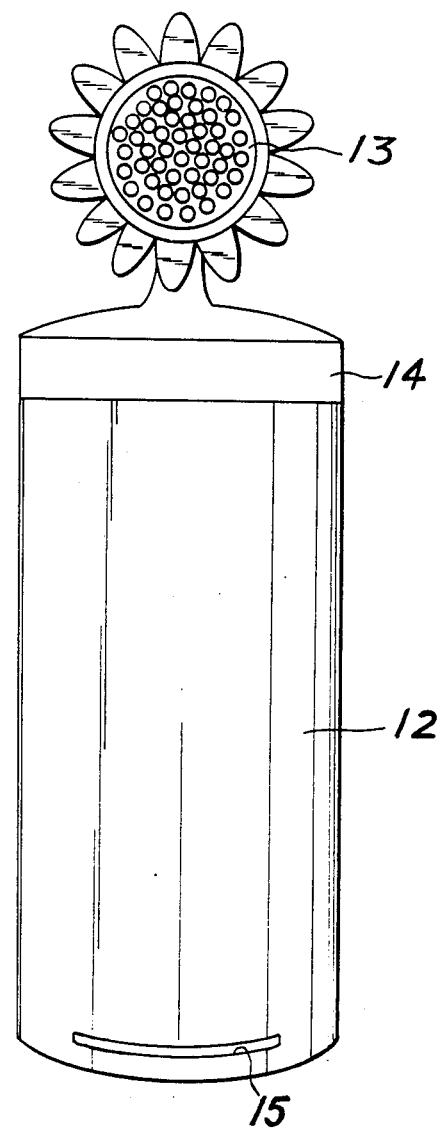

The patterned projection 13 may be of any form as far as it can be engaged with the slit 15. For instance, it may be in the form of the head of cat as shown in FIG. 3 or in the form of a sun flower as shown in FIG. 4.

Figure 5:
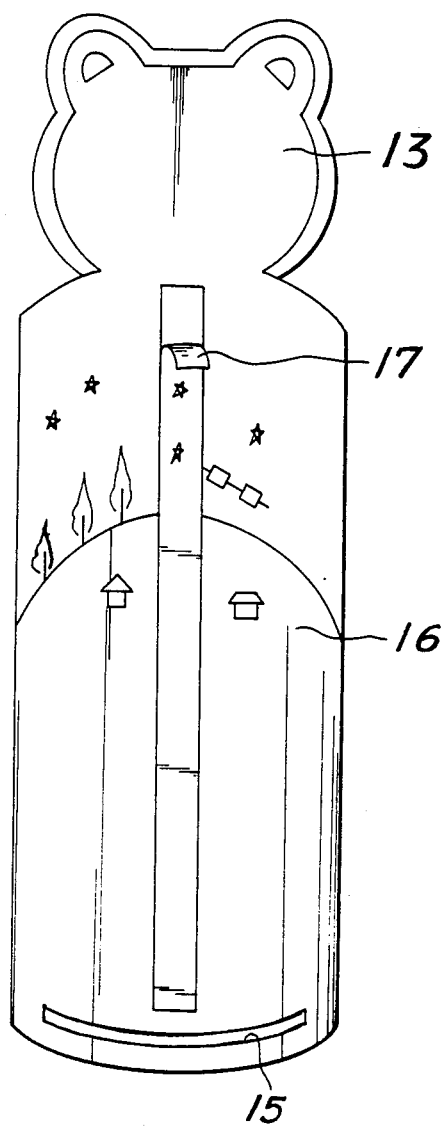
FIG. 5 is a rear view showing a modification of a sanitary napking in accordance with the present invention.

Furthermore, as shown in FIG. 5, an image of a scenery of a fairy tale may be printed over the back side 16 of the sanitary napkin so that melancholy can be dissipated during menstruation.

Moreover, the back side, that is, the portion of the sanitary napkin which does not contact with the body, may have ivory color or other soft and pleasant color so the pleasantness of the used napkin may be maintained. In other words, one is relieved from unpleasant feeling after the use or at the time of disposal.

As shown in FIG. 5, the sanitary napkin may be provided with an adhesive tape 17 so as to prevent the slippage of the sanitary napkin.

Figure 6:
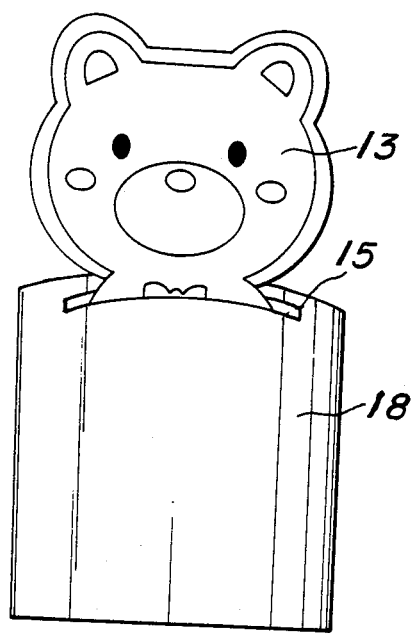
FIG. 6 is an explanatory view used to explain the package of a sanitary napkin in accordance with the present invention.
Figure 1:
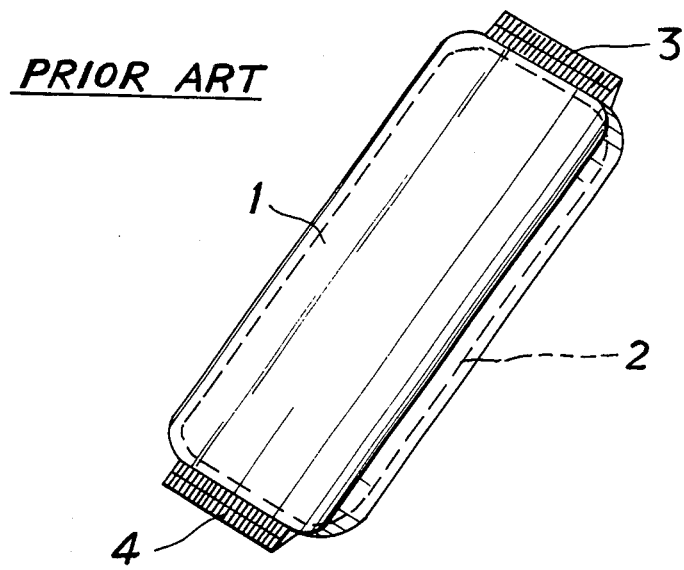
FIG. 1 is a perspective view showing a conventional sanitary napkin.

The sanitary napkin in accordance with the present invention shown in FIG. 2 may be packed in an inner package 18, as shown in FIG. 6, from which the pattern projection 13 extends. As a result, the sanitary napkin has a very pretty appearance. Furthermore, a pretty image picture may be printed or otherwise formed over the back surface 16 of the soft case 12, so that the folded sanitary napkin gives an appearance as shown in FIG. 6.

While the patterned projection 13 has been described on the assumption that a sanitary napkin in accordance with the present invention is used especially by young girls, but it is to be understood that the present invention is not limited to the patterned projections as shown in the accompanying drawings and that various colorful and elegant patterns or images may be provided depending on the ages. Furthermore, the image bearing portion 14 may be used as a medium or space for commercial advertisement. Pleasant images on the image bearing portions 14 can further improve the following advantageous effects of the sanitary napkin in accordance with the present invention.

The effects, features and advantages of the present invention may be summarized as follows:

(1) The patterned projection 13 can relieve unpleasantness during menstruation. That is, melancholy mood may be changed to pleasant mood.

(2) The used sanitary napkin may be folded securely by inserting the patterned projection into the slit, so that the flow attached to the sanitary napkin can be concealed and the used sanitary napkin may be disposed easily and cleanly in a pleasant manner.

(3) The patterned projection may have a combination of a pleasant pattern or image of famous character, each season, words, phrases or the like. Furthermore, it may be used as a commercial advertisement medium in order to promote the sale of sanitary napkin or other goods by using the sanitary napkin as an advertisement medium.

(4) The patterned projection may be varied depending upon the ages; that is, the patterned projection may be varied to provide images which fit to teenagers who experience the first menstruation or menarche and to those at the ages of twenties, thirties and forties, respectively.

What is claimed is:

1. A sanitary napkin comprising:
    an abosorbent pad for absorbing the flow from vagina;
    a soft case for containing said absorbent pad therein, the outer surface of said soft case which does not contact a human body having an image pattern;
    a patterned projection extended from one end of said soft case and bearing a symbolic pattern, said patterned projection being able to be folded; and
    a slit formed in the other end of said soft case, so that the folded patterned projection can be inserted into said slit for fixed engagement with said patterned projection, in a manner that said symbolic pattern and said image pattern appear on the same side, said patterned projection being detachable from said slit.

2. A sanitary napkin as claimed in claim 1, wherein said outer surface is colored with said image pattern.

3. A sanitary napkin as claimed in claim 1, wherein said outer surface of said soft case is provided with an adhesive tape for preventing the slippage of said sanitary napkin.

4. A sanitary napkin as claimed in claim 2, wherein said outer surface of said soft case is provided with an adhesive tape for preventing the slippage of said sanitary napkin.

* * * * *